United States Patent
Schafer et al.

(10) Patent No.: US 8,206,326 B2
(45) Date of Patent: Jun. 26, 2012

(54) COMBINATION ULTRASOUND-PHOTOTHERAPY TRANSDUCER

(75) Inventors: Mark E. Schafer, Lower Gwynedd, PA (US); Brady Aller, West Chester, PA (US)

(73) Assignee: Sound Surgical Technologies, LLC, Louisville, CO (US)

( * ) Notice: Subject to any disclaimer, the term of this patent is extended or adjusted under 35 U.S.C. 154(b) by 624 days.

(21) Appl. No.: 12/189,829

(22) Filed: Aug. 12, 2008

(65) Prior Publication Data

US 2009/0227909 A1    Sep. 10, 2009

Related U.S. Application Data

(60) Provisional application No. 61/033,470, filed on Mar. 4, 2008.

(51) Int. Cl.
*A61H 1/00* (2006.01)
*A61N 5/06* (2006.01)

(52) U.S. Cl. .................................. 601/2; 601/1; 607/88

(58) Field of Classification Search .................. 601/1, 2; 607/88
See application file for complete search history.

(56) References Cited

U.S. PATENT DOCUMENTS

| | | | |
|---|---|---|---|
| 2,283,285 A | 5/1942 | Pohlman |
| 2,830,578 A | 4/1958 | De Groff |
| 3,358,677 A | 12/1967 | Sheldon |
| 3,602,577 A | 8/1971 | Byram |
| 3,828,769 A | 8/1974 | Mettler |
| 4,412,148 A | 10/1983 | Klicker et al. |
| 4,530,360 A | 7/1985 | Duarte |
| 4,658,176 A | 4/1987 | Nakaya et al. |
| 4,683,396 A | 7/1987 | Takeuchi et al. |
| 4,930,504 A | 6/1990 | Diamantopoulos et al. |
| 5,259,380 A | 11/1993 | Mendes et al. |
| 5,316,000 A | 5/1994 | Chapelon et al. |
| 5,358,503 A | 10/1994 | Bertwell et al. |
| 5,520,612 A | 5/1996 | Winder et al. |
| 5,549,544 A | 8/1996 | Young et al. |
| 5,690,608 A | 11/1997 | Watanabe et al. |
| 5,699,804 A | 12/1997 | Rattner |
| 5,913,883 A | 6/1999 | Alexander et al. |
| 6,273,864 B1 | 8/2001 | Duarte et al. |
| 6,290,713 B1 | 9/2001 | Russell |
| 6,361,509 B1 | 3/2002 | Reuner |
| 6,443,978 B1 | 9/2002 | Zharov |
| 6,533,803 B2 | 3/2003 | Babaev |

(Continued)

FOREIGN PATENT DOCUMENTS

CA    2268415 A1    10/2000

OTHER PUBLICATIONS

International Search Report and Written Opinion issued in connection with corresponding International Application No. PCT/US2009/035816, date of mailing Apr. 21, 2009.

*Primary Examiner* — Michael Rozanski
(74) *Attorney, Agent, or Firm* — Sheridan Ross PC

(57) ABSTRACT

A soundhead of a treatment device is provided that enables a volume of tissue located beneath the soundhead to simultaneously receive ultrasound and light stimulation. According to one embodiment, the soundhead includes an ultrasound transducer, a light source, and a faceplate extending across a face of the transducer for providing a tissue contacting and ultrasound energy coupling surface of the soundhead. The faceplate is transparent or translucent to the light generated by the light source. Alternate embodiments including externally mounted light sources are also disclosed.

20 Claims, 11 Drawing Sheets

U.S. PATENT DOCUMENTS

| | | |
|---|---|---|
| 6,702,749 B2 | 3/2004 | Paladini et al. |
| 6,761,729 B2 | 7/2004 | Babaev |
| 7,022,089 B2 | 4/2006 | Ooba et al. |
| 7,090,649 B2 | 8/2006 | Kang |
| 7,195,603 B2 | 3/2007 | Yamazaki et al. |
| 7,273,459 B2 | 9/2007 | Desilets et al. |
| 7,282,036 B2 | 10/2007 | Masuda |
| 2004/0236252 A1 | 11/2004 | Muzzi et al. |

FIG. 4A
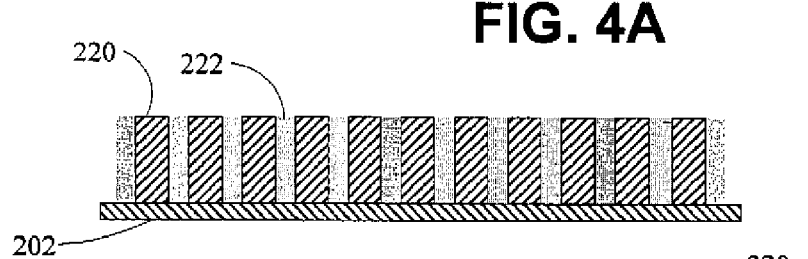
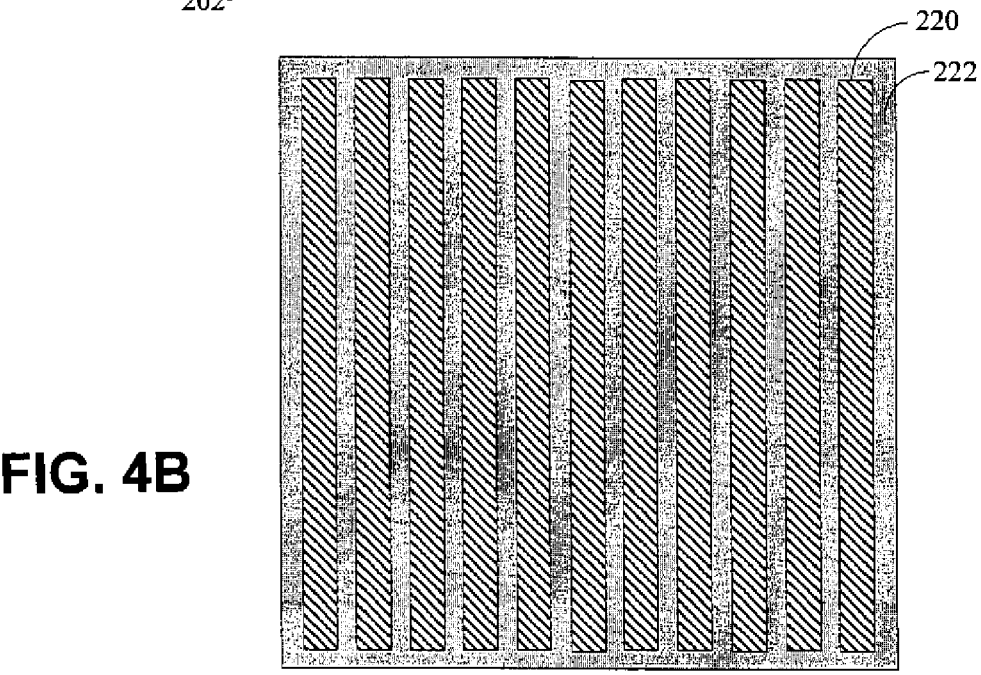
FIG. 4B
FIG. 4C
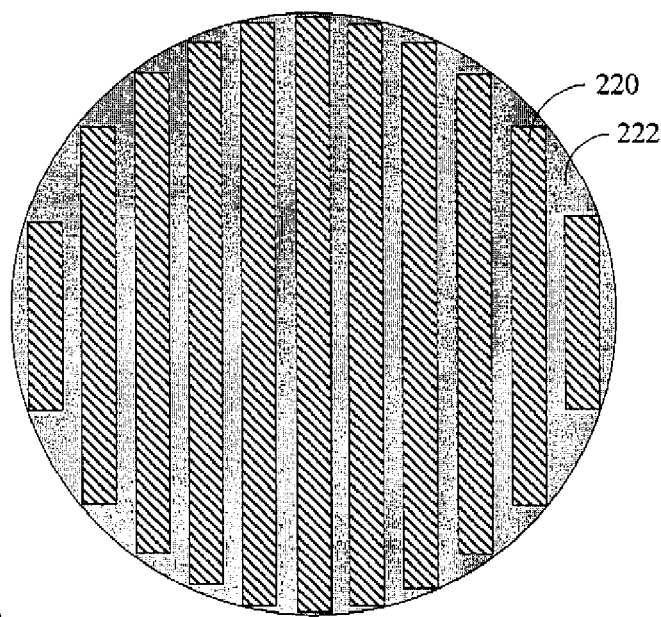

FIG. 7A
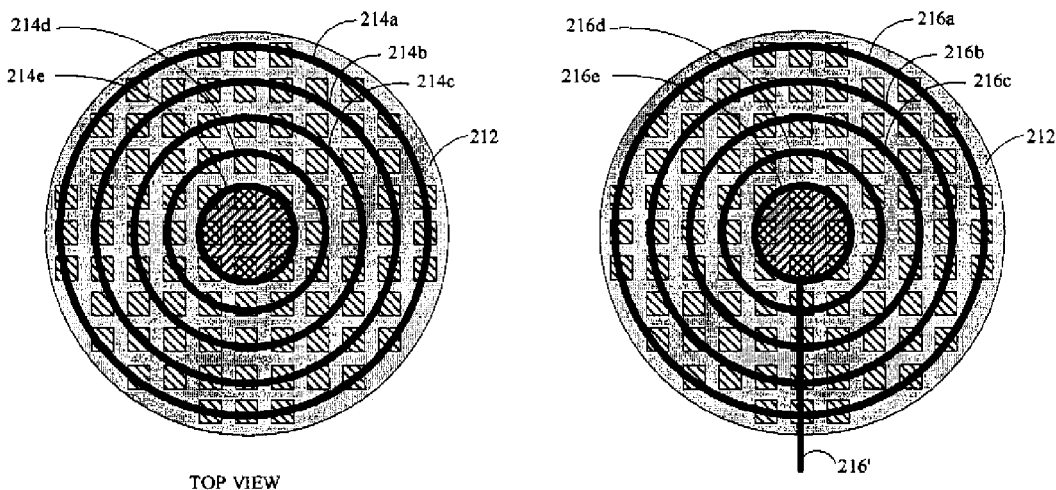
FIG. 7B
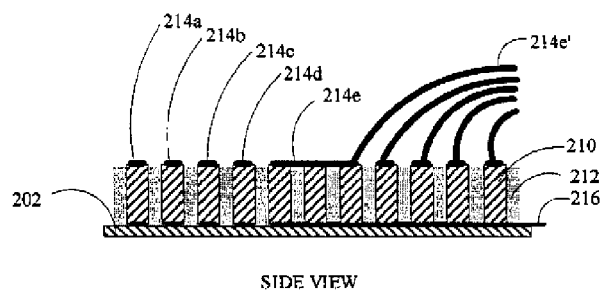
FIG. 7C

FIG. 9A
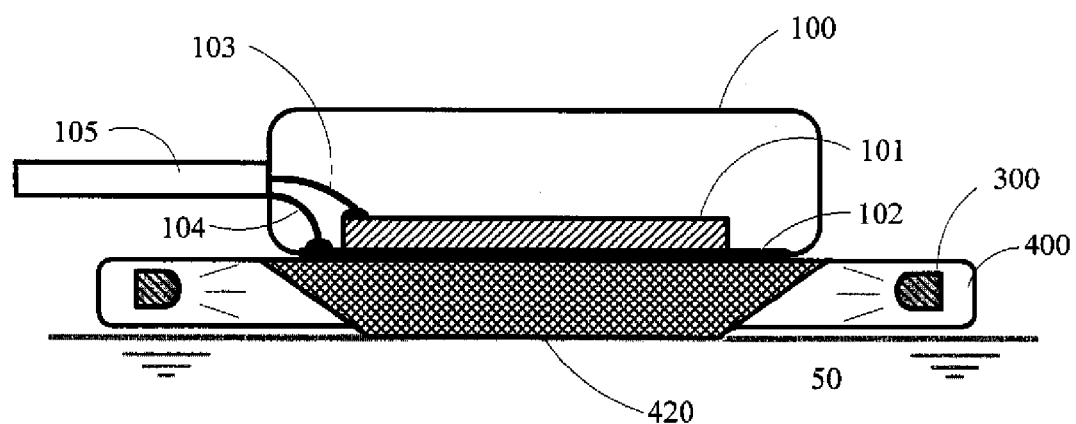
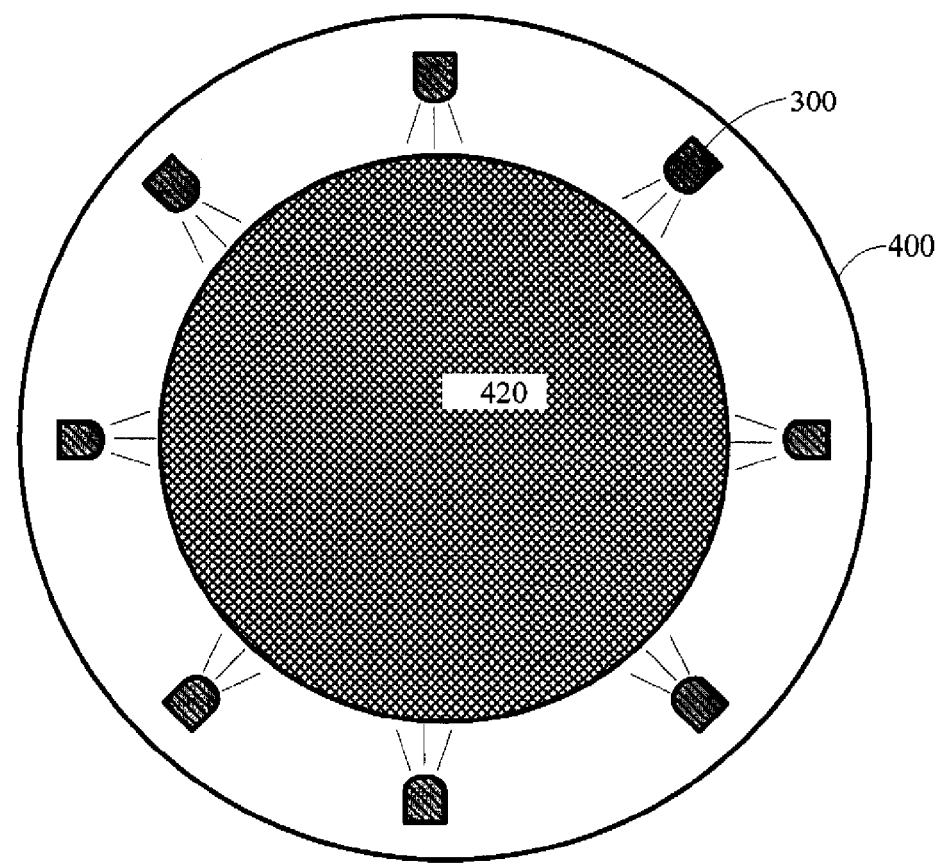
FIG. 9B

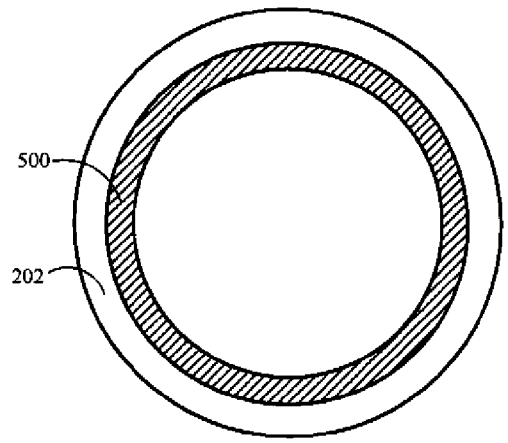 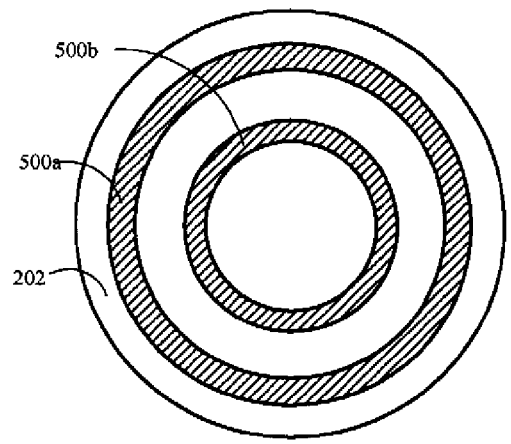
FIG. 11A
FIG. 11B

COMBINATION ULTRASOUND-PHOTOTHERAPY TRANSDUCER

CROSS-REFERENCE TO RELATED APPLICATIONS

This application claims the benefit under 35 USC §119(e) of U.S. Provisional Patent Application No. 61/033,470, filed Mar. 4, 2008.

BACKGROUND OF THE INVENTION

The present invention relates to Ultrasonics, more specifically, to the application of ultrasound energy for physical therapy and wound or tissue treatment.

Ultrasound energy has been used for over 50 years as a therapeutic treatment modality in physical therapy and sports medicine. Recently, lower intensity ultrasound has been used to accelerate the healing of bone fractures and both fresh and long term non-healing wounds. For purpose of example, U.S. Pat. No. 7,282,036 B2 issued to Masuda, U.S. Pat. No. 7,195,603 B2 issued to Yamazaki et al., U.S. Pat. No. 7,022,089 B2 issued to Ooba et al., U.S. Pat. No. 6,273,864 B1 issued to Duarte et al., U.S. Pat. No. 5,690,608 issued to Watanabe et al., U.S. Pat. No. 5,549,544 issued to Young et al., U.S. Pat. No. 5,520,612 issued to Winder et al., U.S. Pat. No. 4,530,360 issued to Duarte, U.S. Pat. No. 3,2828,769 issued to Mettler, U.S. Pat. No. 2,830,578 issued to De Groff, and U.S. Pat. No. 2,283,285 issued to Pohlman disclose various therapy apparatus including handpieces containing ultrasound transducers.

It has also been shown that phototherapy, that is, the application of light at different wavelengths, can have a therapeutic effect on skin and underlying tissue. For example, see U.S. Pat. No. 6,443,978 B1 issued to Zharov, U.S. Pat. No. 6,290,713 B1 issued to Russell, U.S. Pat. No. 5,913,883 issued to Alexander et al., U.S. Pat. No. 5,358,503 issued to Bertwell et al., U.S. Pat. No. 5,259,380 issued to Mendes et al., and U.S. Pat. No. 4,930,504 issued to Diamantopoulos et al. for various phototherapy treatment apparatus.

Accordingly, medical and cosmetic devices have been built and sold which provide for either treatment modality. With respect to ultrasound devices, it is conventional to position the ultrasound transducer behind an opaque, metal front face of the device that directly contacts the skin of the patient. The conventional faceplate and ultrasound transducer covers the tissue region being treated so that light cannot be readily applied to the same area of skin. Thus, the presence of the front face provides an obstacle to the simultaneous application of ultrasound and light to tissue underlying the front face.

Some therapeutic ultrasound systems include separate ultrasound and light sources (e.g. Hill Therapeutics HF54, BTL Physio BTL-4800SL), so that the operator can conveniently switch between the two treatments. Also see U.S. Pat. No. 7,090,649 B2 issued to Kang which discloses a skin management system that includes various separate handpieces capable of performing different functions. Some of the handpieces include light sources and others include an ultrasound transducer. However, it is not possible to treat with both modalities at the same time with these devices, let alone at the same time on the same volume of tissue.

Some prior art systems have used smaller transducers, or "sound heads", such that the separate light source can be applied nearby. However, again, these do not allow for simultaneous stimulation by both ultrasound and light over the same tissue region.

Other systems have included a small light aperture in the middle of the transducer, but for these units, the light source is used not for therapy, but as an adjunct to the diagnostic use of the ultrasound. For example, transducers designed for the purpose of measuring the size of the human eye, called A-scan devices, may have a light emitting from their center, so that the patient can be told to look at the light as the probe is placed on the eye (Paradigm Medical P-2000). In this way, the "fixation light" causes the patient to properly hold their gaze, thus allowing the transducer to make proper contact with the corneal surface. This approach is not considered for any therapeutic application of either the ultrasound or the light. Another similar example is provided by U.S. Pat. No. 6,702,749 B2 issued to Paladini et al. which discloses an optical needle guide for an ultrasound guided needle biopsy.

U.S. Pat. Nos. 6,533,803 B2 and 6,761,729 B2 issued to Babaev disclose a handpiece of a treatment device used to deliver a spray of liquid drugs and laser energy to a wound. In use, the handpiece is positioned a spaced distance (about 0.1 inch) from the wound and is activated to simultaneously apply a spray of atomized particles of a drug delivered via ultrasonic waves and a beam of light to the wound.

U.S. Pat. No. 5,699,804 issued to Rattner discloses an apparatus having an X-ray transparent ultrasound transducer provided as a piezoelectrically activated polymer (PVDF) foil, and U.S. Pat. No. 6,361,509 B1 issued to Reuner discloses a similar device that includes sources for generating acoustic and light waves. The light source emits a focused beam of visible light along the acoustic wave axis for the purpose of making the acoustic axis visible.

U.S. Patent Application Publication No. 2004/0236252 A1 of Muzzi et al. discloses apparatus for treating cellulitus. The apparatus includes a handpiece having a face plate adapted to contact the skin of a patient and provide mechanical message via pulsed suction through a central open channel that extends through the face plate. Simultaneous with the pulsed suction, biostimulation is provided via six laser diodes distributed uniformly on the face plate around the channel opening.

Finally, U.S. Pat. No. 7,273,459 B2 issued to Desilets et al., U.S. Pat. No. 5,316,000 issued to Chapelon et al., U.S. Pat. No. 4,683,396 issued to Takeuchi et al., U.S. Pat. No. 4,658,176 issued to Nakaya et al., and U.S. Pat. No. 4,412,148 issued to Klicker et al. disclose composite piezoelectric transducers in general.

SUMMARY OF THE INVENTION

The present invention combines a new transducer design approach of composite piezoelectric transducers, specifically designed to allow light to pass through them, with a photo applicator source mounted behind the transducer, but within the probe head. This allows the light energy from the light source to pass through the ultrasound transducer and into the tissue, while the ultrasound transducer applies ultrasound energy simultaneously to the tissue. The light source can be an LED, laser diode, or the like.

Commercial devices on the market have not solved this problem directly, but have provided for independent acoustic and optical sources (handpieces) powered from the same console. Conventional systems have relied on conventional piezoelectric transducer technology, which generally includes a solid metal front face (the side which faces the patient).

BRIEF DESCRIPTION OF THE DRAWINGS

The foregoing and other objects, features and advantages of the present invention should become apparent from the following description when taken in conjunction with the accompanying drawings, in which:

FIGS. 4A-4C are cross-sectional and top plan views of an alternate structure of the piezocomposite transducer according to the present invention;

FIGS. 7A-7C are a top plan view, a bottom plan view, and a cross sectional view of an alternate embodiment of the present invention, one which provides for an annular array of sub-elements;

FIGS. 9A-9B is a cross-sectional and plan view of an alternative embodiment according to the present invention which includes a light source that is disposed around the rim of an ultrasound transducer;

FIGS. 11A-11B are top plan views of alternative embodiments having one or more ring transducer elements.

DETAILED DESCRIPTION OF THE PRESENT INVENTION

Figure 1A:
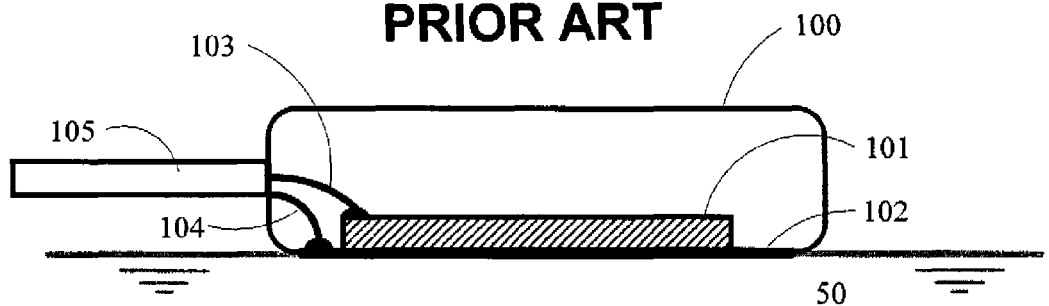
FIGS. 1A-1C are cross-sectional and bottom plan views of the construction of an ultrasound scanhead according to the prior art.
Figure 1B:
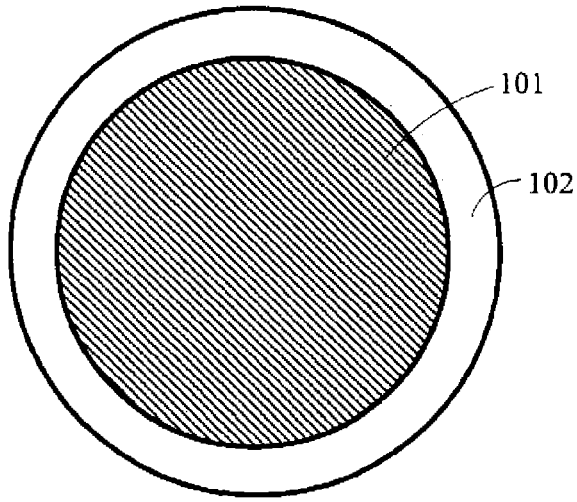
Figure 1C:
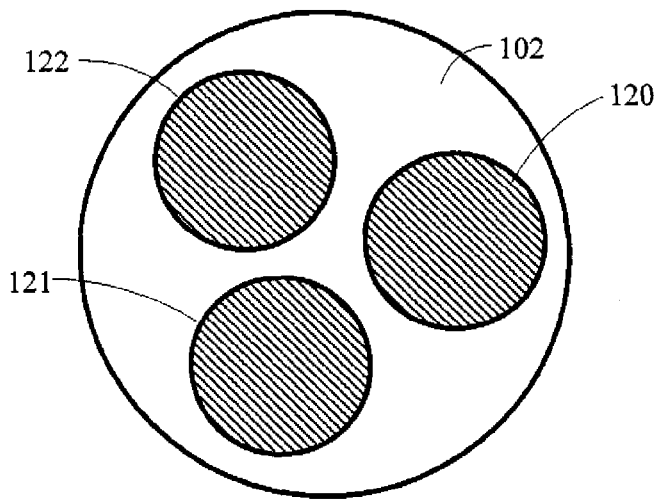

FIGS. 1A-1C depict a soundhead of design typical of the prior art. FIG. 1A is a simplified cutaway diagram of the soundhead in contact with tissue 50. The scanhead consists of housing 100, which contains the ultrasound transducer element 101, attached to the faceplate 102 which makes contact with tissue 50. The faceplate 50 is typically metal, either stainless steel or aluminum. Cable 105 attaches to housing 100. Lead 103 of cable 105 attaches to the rear of transducer element 101, and lead 104 of cable 105 attaches to the front of transducer element 101, typically through an electrical connection to the metal faceplate 102. Other means of connection have been used, including "wrap around" electrodes on transducer element 102 such that the electrical connection to the front of the transducer element is brought around to an isolated portion of the rear of the transducer element. The exact means are not necessarily important to the present invention.

The current art in ultrasound therapy uses soundheads operating at frequencies between 1 and 5 MHz, with 1 and 3 MHz being the most popular. The size of the scanhead ranges from 20 mm to 50 mm in diameter, depending upon the region of the body to be treated.

Transducer element 101 is typically a solid, continuous piece of piezoceramic material, as can be purchased from a number of vendors (e.g. Morgan Electro Ceramics, Bedford, Ohio). Most typically it is furnished as a circular disk, as can be seen in FIG. 1B. This approach is relatively low cost and robust.

FIG. 1C depicts another embodiment of the prior art, in which the single transducer element 101 attached to faceplate 102 is replaced by three smaller elements 120, 121, and 122, all still attached to faceplate 102. This design is sometimes employed to modify the structure of the ultrasonic beam emitted into tissue 50. The modification may be desirable in some instances to control the unwanted focusing of the ultrasound energy.

Figure 2A:
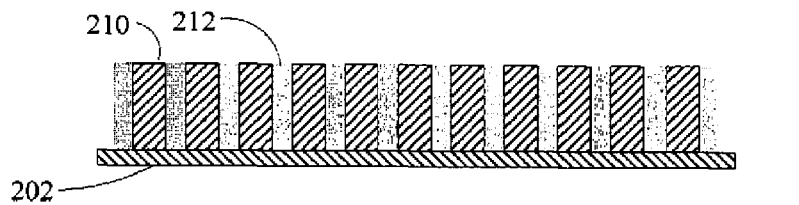
FIGS. 2A-2C are cross-sectional and top plan views of the structure of piezocomposite transducers according to the present invention.
Figure 2B:
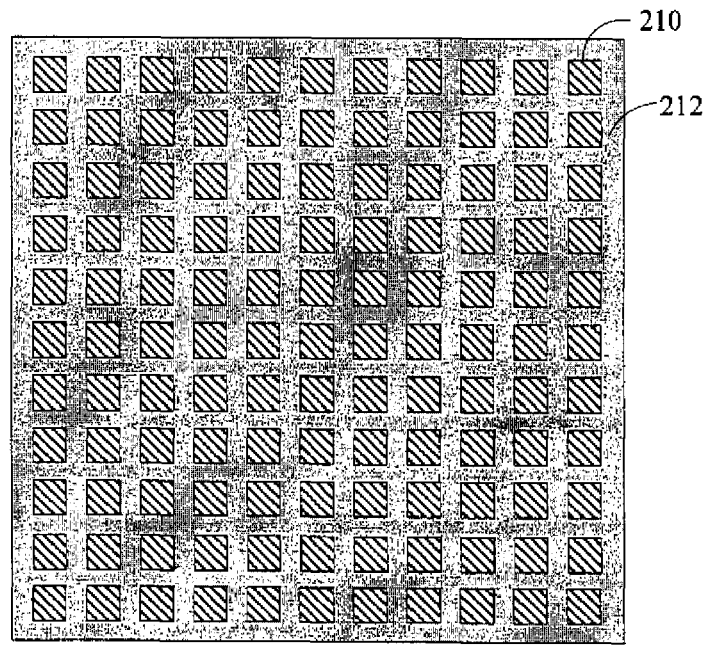
Figure 2C:
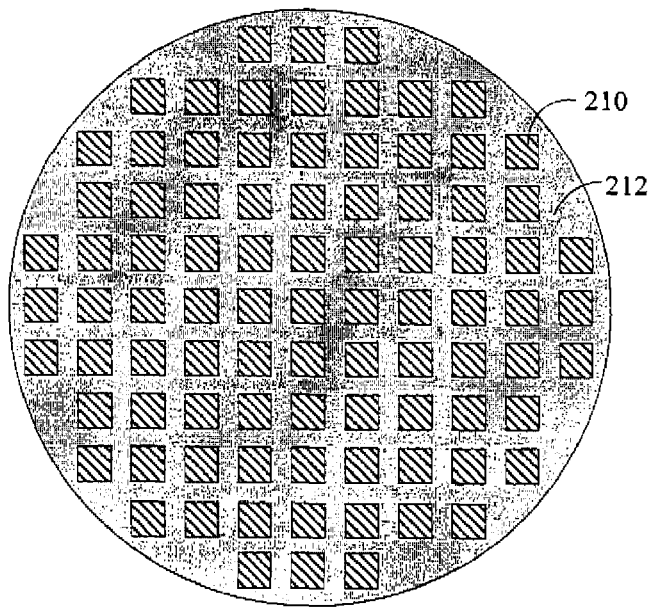

FIGS. 2A-2C depict transducer structures according to the present invention and are comprised not of a single continuous element, but of a plurality of smaller individual elements 210. This approach is known as a piezocomposite, because it is a composite of individual elements 210, imbedded or surrounded by a polymer matrix material 212. This approach has been known for a number of decades. See, for example: R. E. Newnham et al., "Composite Piezoelectric Transducers", Materials in Engineering, vol. 2, December 1980, pp. 93-106; T. R. Gururaja et al., "Piezoelectric Ceramic-Polymer Composites For Transducer Applications", Electronic Ceramics, 1987, pp. 92-145; H. P. Savakus et al., "PZT-Epoxy Piezoelectric Transducers" Materials Research Bulletin, vol. 16, 1981, pp. 677-680; U.S. Pat. No. 4,412,148 issued to Klicker et al.; U.S. Pat. No. 4,658,176 issued to Nakaya et al.; and U.S. Pat. No. 4,683,396 issued to Takeuchi et al. The structure has the advantage of improved performance at lower weight when compared to a solid ceramic transducer at the same frequency and size. This approach is known in the art as a "1-3" composite, because the transducer ceramic material exhibits connectivity only along one axis (giving rise to the "1"), while the polymer matrix material exhibits connectivity along all three axial directions (giving rise to the "3"). The ceramic connectivity is always listed first, followed by the polymer matrix connectivity.

FIG. 2A is a schematic cutaway view of a piezocomposite transducer, with elements 210 imbedded in a matrix material 212, attached to a faceplate 202. FIG. 2B shows a schematic top view of said piezocomposite transducer, showing the relative placement of the individual sub-elements 210. FIG. 2C depicts the application of this approach to a circular aperture configuration.

To date, this type of transducer is commonly found in diagnostic ultrasound equipment, where the increased cost of manufacture is balanced by the much improved performance afforded by the design. In designing these transducers for said diagnostic or therapeutic purposes, the choice of the polymer matrix material 212 and the front face material 202 are determined solely by their ultrasonic properties, and not their light transmission properties.

Figure 3:
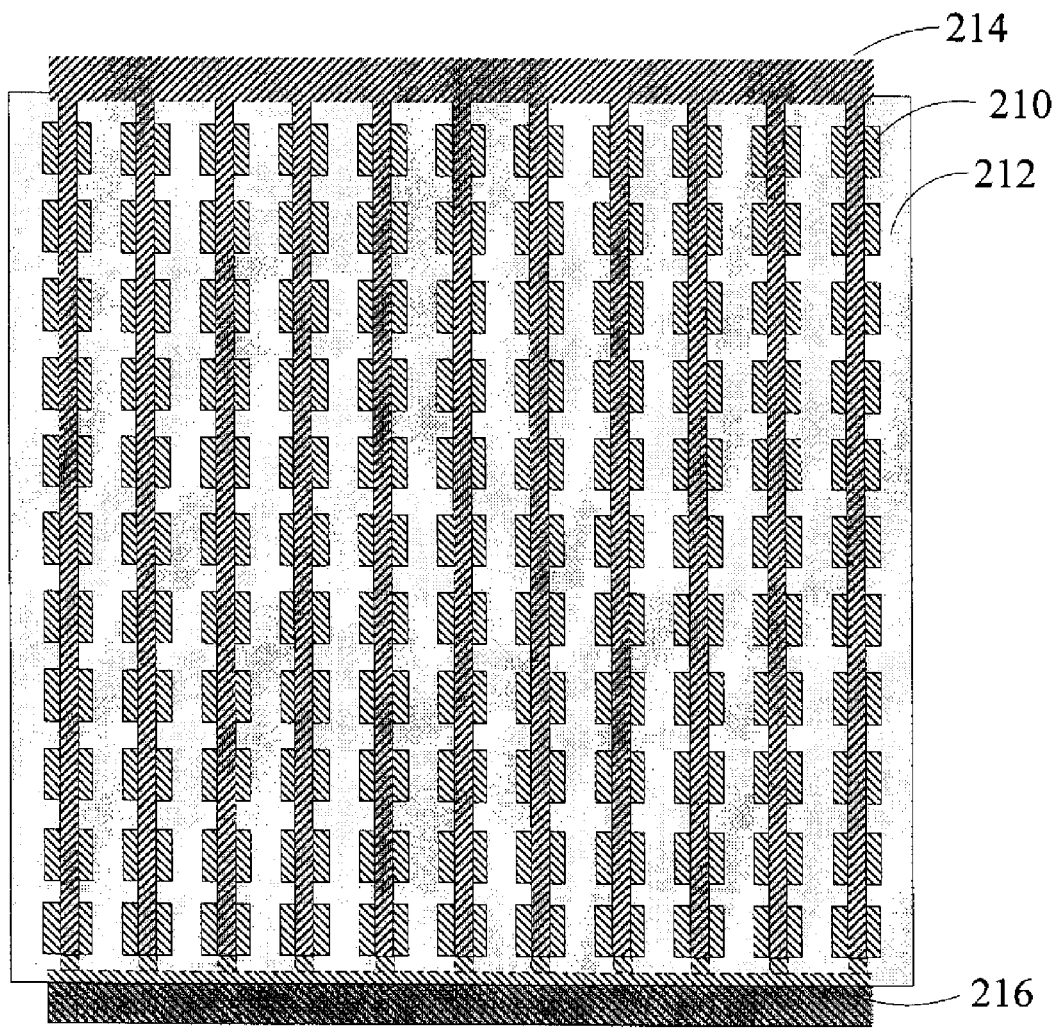
FIG. 3 is a top plan view of means to provide electrical connections to the piezocomposite transducer of the present invention.

FIG. 3 depicts a novel means of the present invention for establishing electrical contact with the individual elements 210 of the 1-3 composite material. The electrodes on the top 214 and bottom 216 may be applied by a silk screening, electro-etching, or plasma sputtering operation. In most diagnostic transducers where light transmission is not a design requirement, these electrodes are typically applied in a plating operation and cover the entirety of the top and bottom surfaces of the transducer. The electrode material may be silver, copper, gold, or other highly conductive material, depending upon the method used for its application. It is important to note the specific design goal of the present invention is to provide for light transmission through the ultrasound transducer structure, so it is important that the electrode material have gaps so as to allow light to pass through the electrodes.

FIGS. 4A-4C depict an alternate embodiment of the present invention which uses a "2-2" connectivity of the transducer ceramic and polymer matrix. The individual elements 220 imbedded in a polymer matrix material 222 are now in the form of bar structures rather than post structures. This approach results in a higher overall volume fraction of ceramic, which leads to a higher acoustic output on transmit. Again, as can be seen in FIGS. 4B and 4C, the overall shape of the transducer may be rectangular, circular or other shapes as the situation demands.

Figure 5:
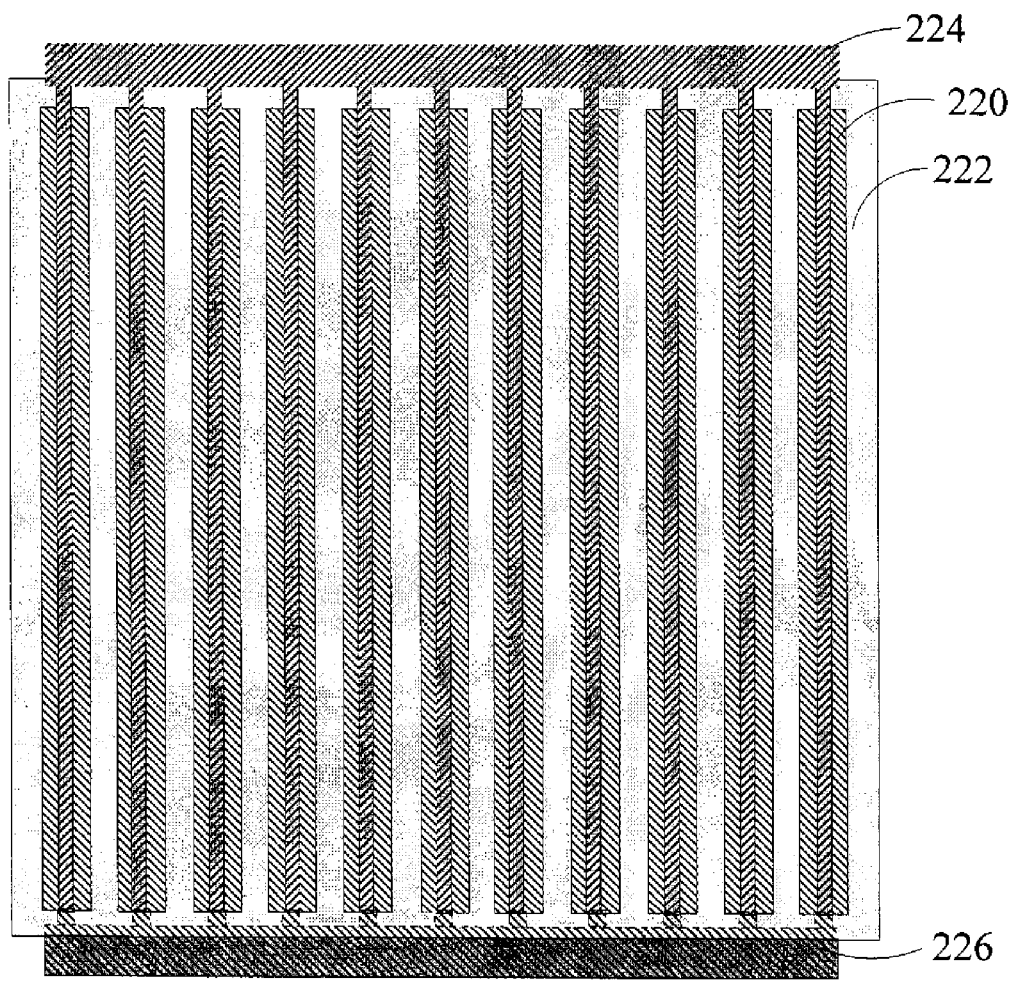
FIG. 5 is a top plan view of a means to provide electrical connections to the alternate piezocomposite transducer structure of the present invention.

FIG. 5 depicts a means for establishing electrical contact with the individual elements 220 of the 2-2 composite material. Electrode 224 is on the top of the structure and electrode 226 is on the bottom, and may be applied by the methods enumerated above. Note that the 2-2 design is more efficient in the balance of light transmission and transducer area, in that with the 1-3 design, the area between some elements may be blocked by the presence of the electrode material. In the 2-2 design, the electrode and ceramic are co-extant.

Figure 6:
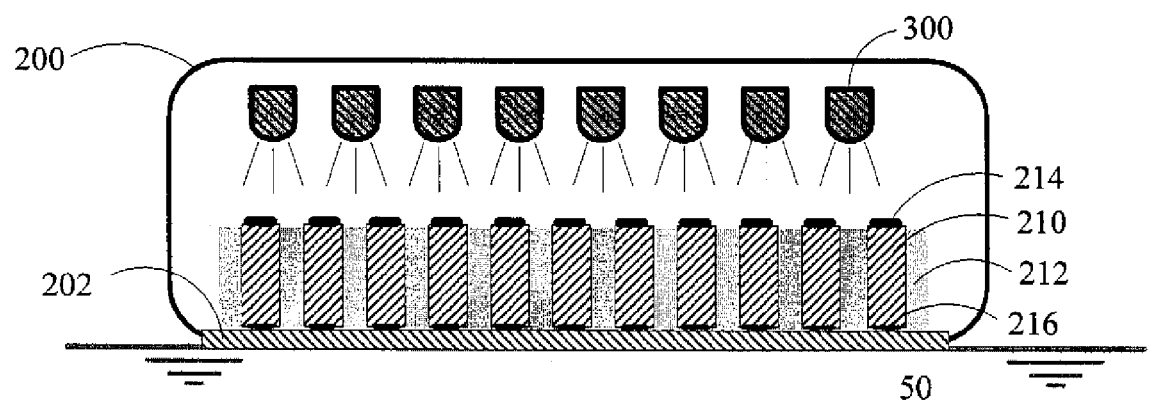
FIG. 6 is a cross sectional view of the overall structure of the treatment device according to the present invention, showing both the ultrasound transducer structure and light sources located behind the transducer structure.

FIG. 6 depicts in schematic form the overall structure of the treatment device of the present invention, with transducer elements 210 imbedded in polymer 212, connected by electrodes 214 on the top and 216 on the bottom, bound to faceplate 202 in contact with tissue 50, contained within housing 200, and transilluminated by a plurality of light sources 300. By choosing the polymer matrix material 212 to have both acceptable acoustic properties and good light transmission properties (e.g. Epotek 310, Epoxy Technology, Billerica Mass.), it is possible to have the tissue 50 beneath the scanhead receive simultaneous ultrasound and light stimulation.

FIGS. 7A-7C depict in schematic form alternate embodiments of the 1-3 composite design, demonstrating alternatives which may be implemented using the methods taught by the present invention. In FIG. 7A, electrodes 214a, 214b, 214c, 214d, and 214e create concentric ring patterns of elements 210. By changing the phase of the electrical drive signals to each ring, it is possible to focus or defocus the resultant ultrasound distribution pattern within the tissue. There may be cases in which the ultrasound is required to be focused in order to achieve a desired minimum ultrasound excitation level within a small volume of tissue. Or it may be desirable to insonify a larger volume of tissue at a lower ultrasound exposure level. Note that electrode 214e also comprises a circular area, which may limit the overall light transmission. FIG. 7B depicts the connections to the bottom side of the transducer element. Here all electrodes 216a-216e are connected to a common electrode 216'.

FIG. 7C shows a side view of the connection scheme, with each ring electrode on the top portion connected via a lead or wire from the rear of the transducer, e.g 214e'. The cable to this transducer would consist of multiple connections which would allow the individual rings to be phased as noted.

Figure 8:
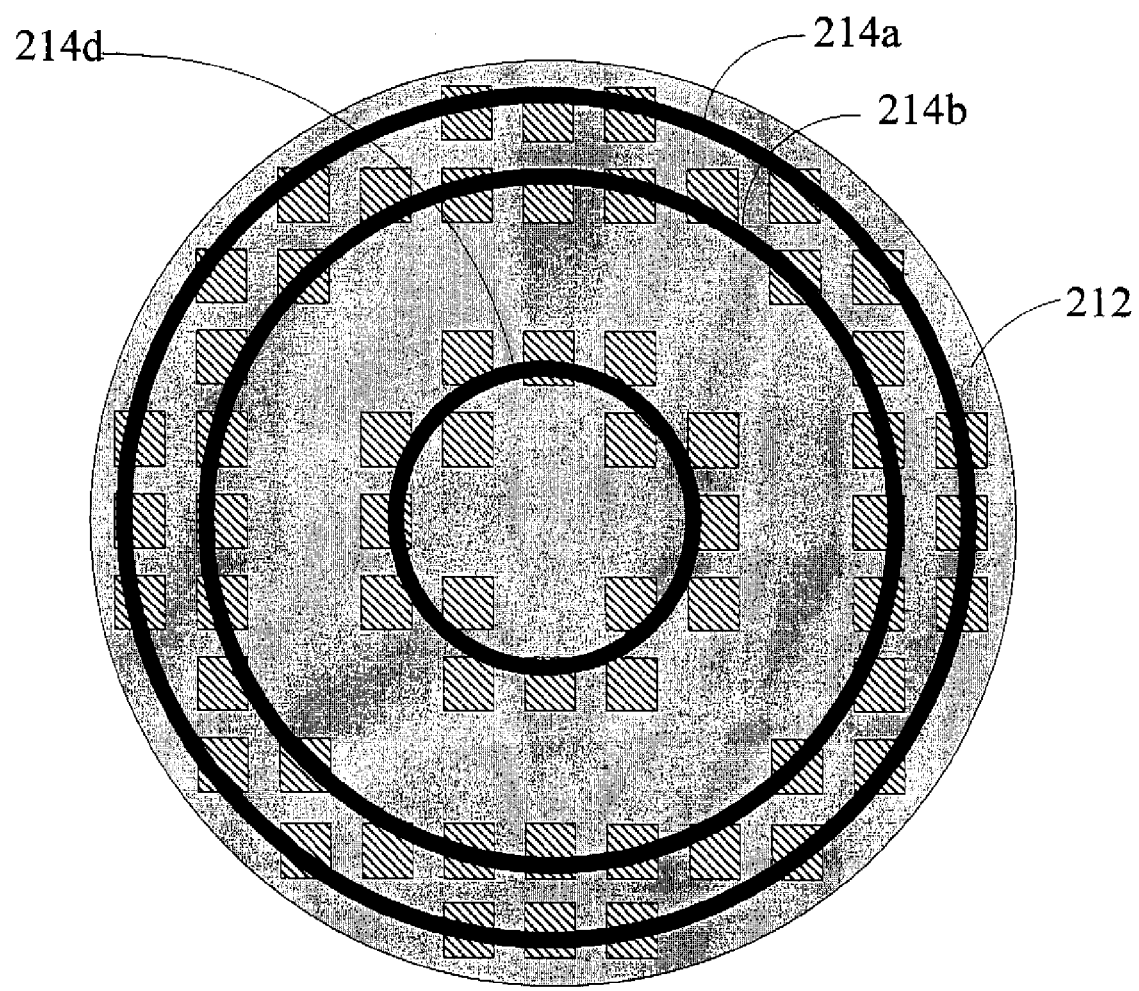
FIG. 8 is a top plan view of an alternate embodiment having an annular array of sub-elements with a selected amount of ultrasound elements removed in order to allow more light to pass through the transducer.

FIG. 8 depicts an example in which selected ultrasound elements have been removed from that shown in FIG. 7A in order to allow more light to pass through the transducer. The elements can be removed in the processing stage before the addition of the polymer/epoxy matrix material. Electrodes 214a, 214c, and 214d may all be connected together electrically, or may be energized separately as noted above. In this case, electrode 214d is only a circular ring, and not an entire disk. The individual rings may be connected as previously depicted in FIGS. 7A-7C.

FIGS. 9A and 9B depict an alternative approach which also permits at least some overlap of the ultrasound beam and a light from a light source disposed around the rim of the ultrasound transducer. This approach would be suitable as a retrofit to an existing ultrasound transducer of the prior art. An opto-acoustic material 420 is interposed between the faceplate 102 of a soundhead of the prior art and the tissue surface 50. Disposed around the periphery of said opto-acoustic material is a plurality of light sources 300 within a housing 400. The opto-acoustic material 420 provides acoustic coupling for the ultrasound energy from the transducer 101. It also reflects the light energy from the light sources 300 downward towards the tissue. This may be done by simple diffusion, e.g. by using a translucent material, or diffuse reflection, e.g. introducing light reflecting particles such as gold or silver particles within the material. This may be done if the material 420 is formed as a cast material, for instance as a mixture of fine gold particles dispersed within a cast epoxy.

Figure 10:
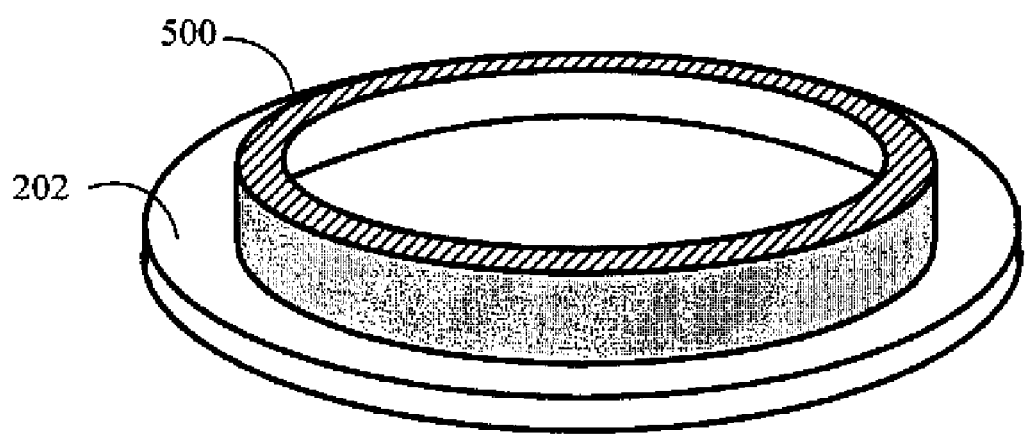
FIG. 10 is a perspective view of an alternative embodiment of the present invention that uses a ring transducer element to excite the front face layer, and allows maximum light transmission.

FIG. 10 depicts an alternative embodiment wherein the balance of light and ultrasound output emphasizes light output. The transducer element is in the form of a ring 500. Such transducer elements are known to those skilled in the art and may be obtained from a number of suppliers (e.g. Morgan Matroc, Ohio). Transducer elements in this form have been used to drive, for instance, ultrasonic surgical equipment. The thickness of the element sets the resonant frequency of the device. One advantage of this approach is that the entire center is available for light transmission through the front face 202. A device built on this principle can be structured similarly to that shown in FIG. 6, with illumination elements 300 positioned directly behind front face 202. This approach has the advantage of structural simplicity, and potentially high light output. However, the ultrasound output which may be obtained with this approach is not as high as that obtained with the other transducer configurations disclosed, nor is the ultrasound field as uniform in the region directly in the center of the transducer. The front face 202 may be considered as a radiating face, like a drum head, depending upon frequency. The higher the frequency, however, the more the ring element 500 will produce an annular region of ultrasound exposure, with less intensity in the center region.

FIGS. 11A and 11B depict the above mentioned alternative embodiment and includes one or a plurality of ring transducer elements. FIG. 11B shows only two elements, 500a and 500b, but those skilled in the art would appreciate that additional elements are possible. These elements could be wired in a manner similar to that shown in FIGS. 7A-7C and 8.

The primary functional difference between the present invention and the prior art is the capability to have light pass through the transducer element, allowing for simultaneous ultrasound and light stimulation of a tissue volume. The structural difference is the use of piezocomposite transducer technology, with the additional design constraints of 1) using a polymer or epoxy matrix material which is transparent or sufficiently translucent; 2) using a transparent or sufficiently translucent front plate rather than a solid metal plate; 3) using a specific pattern of electrodes which provide connection to the individual ultrasound elements within the piezocomposite but also minimize the optical shadowing of the light sources.

Although as noted, there are ultrasound transducers with a small aperture in the center for a "fixation" light, this type of transducer is not designed for a combination therapy. The fixation light is used through a small hole, on the order of several millimeters in diameter. This hole is drilled through the transducer assembly. Other transducers have been designed with holes in or around the transducer face: for instance, transducers used with biopsy needles have holes or slots in them to accommodate the needle. All these transducers are designed for diagnostic purposes and are not intended to have a therapeutic use. Those persons familiar with these devices, e.g. those involved in ophthalmic ultrasound, are not generally aware of the potential need to apply phototherapy and ultrasound therapy to the same tissue volume simultaneously.

Another issue is the fundamental design of the ultrasound transducer. Those skilled in the art of therapeutic transducers have long used metal front face transducers in order to provide: 1) electrical shielding and grounding for patient safety (although some systems have been described which apply an electrical current through the soundhead to provide ancillary electrical stimulation therapy); 2) heat sinking capacity to reduce any unwanted heat generated by the transducer element within the soundhead; and 3) to provide some mechanical stability to the solid ceramic transducer when it is operated at a high drive level. In many current ultrasound therapy devices, the goal is to create deep heating within the tissue bed. Thus the ultrasound powers are relatively high, especially in comparison to diagnostic ultrasound power output levels. To obtain these levels, the metal front face is recommended for the reasons given above, especially with regard to heat capacity of the soundhead and the mechanical stability requirements.

Further, piezocomposites have not been extensively used for high ultrasound output. Because while the design offers certain advantages, especially with regard to the bandwidth of the transducer and coupling of the ultrasound energy, the mechanical losses inherent in the polymer/epoxy matrix absorb too much of the available energy, reducing their efficiency at high drive levels. This inefficiency causes heating within the transducer, which can degrade the polymer/epoxy matrix material.

However, it has been shown that beneficial tissue response can occur at much lower levels of ultrasound stimulation. For example, see U.S. Pat. No. 4,530,360 issued to Duarte and U.S. Pat. No. 5,520,612 issued to Winder et al., where the level of ultrasound intensity is less than 100 mW/cm$^2$ and on the order of 30 mW/cm$^2$. This obviates the need for high transducer drive levels, and thus it is not necessary to use a metal front face. Further, these lower ultrasound levels are compatible with piezocomposite transducer designs.

However, the most critical insight is the intimate knowledge of the design of piezocomposite transducers. Knowing the pattern of ceramic elements imbedded in a polymer/epoxy matrix allowed for the design concept of using a transparent or translucent matrix material. In practice, a translucent material, especially for the front face, would better diffuse the treatment light energy, allowing for more uniform coverage. The trade off is in the amount of total light to reach the skin or tissue surface.

Localized treatment using light sources (also known as topical photodynamic therapy, PDT) has developed into an established modality for a number of conditions, including non-melanoma skin cancers, acne and photorejuvenation. These therapeutic devices use low level lasers (LLLT) or bright light emitting diodes (LEDs) of different colors (wavelengths). Those skilled in the art of such devices are generally not aware of the capabilities of ultrasound for tissue treatment, and are specifically not aware of the possibility of modifications to the ultrasound transducer as have been described herein.

As noted above, the primary advantage of the disclosed invention is the ability to treat tissue with both ultrasound and light at the same time, at the same location. This affords new treatment possibilities, including the synergistic treatment of different diseases. As an example, both ultrasound and light have been demonstrated to have a positive effect on wound repair. Although the complete mechanisms of repair are not completely known, there are indications that ultrasound and light affect different tissue structures, which would lead to the possibility of complementary effects when the two modalities are combined.

Another possibility is the use of ultrasound to change the permeability of skin or other tissue. This would allow topical application of drugs to more efficiently travel to their target tissues. As an example, 5-aminolevulinic acid (5-ALA) is used topically in the treatment of non-melanoma skin cancers. 5-ALA is converted inside the cell into protoporphyrin IX (PPIX), a natural photosensitiser that is usually present in too small a quantity to cause photosensitivity. When 5-ALA is applied to the surface of skin tumors it is preferentially absorbed and converted by dysplastic/neoplastic cells. When these cells are treated with light therapy, the resulting photodynamic reaction produces reactive oxygen species, leading to cell death. Ultrasound could accelerate the uptake process by increasing the permeability of the cell walls.

Another advantage of the invention disclosed herein is the use of a non-metallic front face material. While the metal front face does have some advantages for high power ultrasound applications, it is actually a very poor choice as a coupling material between the transducer and the skin. This is because the acoustic impedance of the metal is higher than the ceramic material, which causes an impedance mis-match. This causes ultrasound energy to be reflected back into the transducer element, lowering overall efficiency. Ideally, the front face should be an acoustic matching layer, such that its acoustic impedance lies between that of the transducer and the tissue. The principles of acoustic matching layers are well known (cf F. Kremkau, "Diagnostic Ultrasound: Principles and Instruments", 6$^{th}$ Ed. ISBN 0-7216-9330-X, 2002, pp. 66). Plastic materials such as Lucite® are both transparent and acoustically suitable for use as a front face material. There are design tradeoffs with the front face in terms of the light attenuation as a function of light wavelength, accelerated aging of materials due to light exposure, etc. which will be obvious to those skilled in the art of plastics usage. To these requirements is the additional design requirement, as noted, of acoustic matching. Again, those skilled in the art of transducer design are aware of the needs for the proper material, thickness, bonding, etc.

Another advantage of the invention herein disclosed is the capability of shaping the front of the transducer into a non-planar form. Because the piezocomposite is made from individual elements, especially in the case of the 1-3 design, it is possible to shape the overall structure into a spherical cap, either concave (which is often done in diagnostic imaging to impart focusing properties) or convex (which would allow for the dispersion of the ultrasound over a wider area). It would also allow the photo-ultrasound transducer to be shaped into novel configurations, such as into a cylindrical shape. Such a shape could be used, for instance, for treatment within body cavities.

Another advantage of the design is to further combine the utility of the ultrasound with a light source and use the ultrasound transducer not only as a treatment device but also as a diagnostic device. Specifically, the ultrasound transducer could be used for imaging a portion of the tissue. Moreover, the ultrasound transducer could be employed using Doppler principles (cf F. Kremkau, Chapter 5) to monitor bloodflow in the tissue. This could be employed in combination with a light source or ultrasound therapy to determine an increase or decrease in bloodflow to a tumor region in response to said therapy. The individual transducer electrodes, as described in FIGS. 7A-7C or FIG. 8, could allow for Continuous Wave Doppler monitoring. The single electrode pattern 224 shown in FIG. 5 could be subdivided into individual rows, allowing the ultrasound beam to be electronically steered (cf Kremkau, Chapters 3 and 4).

With respect to the alternative design depicted in FIGS. 9A and 9B, this approach would be applicable as a retrofit to an existing transducer soundhead. Ultrasound coupling gel would be used between the faceplate 102 and the opto-acoustic material 420. The design of the material 420 is at the choice of the designer, and may be comprised of a series of internal optical reflectors, each sufficiently thin so as to be nominally transparent to the ultrasound beam. For example, gold foil in thicknesses of less than 50 micron, cast into a clear resin in a conical fashion would reflect much of the light from sources 300, while causing minimal effect on the ultrasound beam. While this approach would not have the advantages of the design described above, including complete overlap of the ultrasound and light beams, uniformity of the ultrasound and light beams, capability of shaping the transducer surface, etc. it does allow for retrofitting existing soundheads, which can afford a commercial advantage.

With respect to the alternative design depicted in FIGS. 10, 11A and 11B, this approach would be a lower cost alternative to the piezocomposite design, and would, depending upon the number of rings used, allow more light to pass through. It would, however, generally produce an ultrasound field with lower intensity and with less uniformity that the approaches described earlier. Thus the designer has a number of choices to balance with these various design approaches. The more that the surface area of the transducer is taken up with ultrasound elements, the lower the light output, but the higher and more uniform the ultrasound. The 1-3 composite approach can, at best, have only 75 percent of the possible light output of an equivalent area filled only with lighting elements; the 2-2 approach, is even more limited, with around 50 percent (depending upon the ratio of the transducer element width to the element-to-element spacing). It is clear to those skilled in the art that these ratios can be changed to adjust the ultrasound output and the light output as the demands of the clinical situation dictate. The invention disclosed herein affords the designer great flexibility in meeting the clinical requirements for simultaneous, co-located ultrasound and phototherapy treatment.

While preferred treatment devices have been described in detail, various modifications, alterations, and changes may be made without departing from the spirit and scope of the present invention as defined in the appended claims.

The invention claimed is:

1. A soundhead that allows a volume of tissue located beneath the soundhead to simultaneously receive ultrasound and light stimulation, the soundhead comprising:
    an ultrasound transducer for generating ultrasound to treat the volume of tissue;
    a faceplate extending across a face of said transducer and configured to provide a tissue contacting and ultrasound energy coupling surface of the soundhead;
    a topical photodynamic therapy light source for producing light that has a therapeutic effect to treat the volume of tissue, the light comprising at least one of visible light, ultraviolet light and infrared light, said light source being located on a same side of said faceplate as said ultrasound transducer, wherein said faceplate is transparent or translucent to said light produced by the topical photodynamic therapy light source.

2. A soundhead according to claim 1, wherein said ultrasound transducer has an opening extending there through, wherein said faceplate is made of a material that is transparent or translucent to said light produced by the topical photodynamic therapy light source, and wherein said light source is located within or adjacent said opening.

3. A soundhead according to claim 1, wherein said light source is located adjacent a face of said ultrasound transducer opposite said faceplate such that said ultrasound transducer extends between said light source and said faceplate.

4. A soundhead according to claim 3, wherein said ultrasound transducer includes at least one ultrasound transducer element embedded within a matrix material, and wherein said matrix material is transparent or translucent to the light produced by said topical photodynamic therapy light source.

5. A soundhead according to claim 4, wherein said ultrasound transducer includes a plurality of separate, spaced-apart ultrasound transducer elements embedded within said matrix material.

6. A soundhead according to claim 5, wherein said transducer is a piezocomposite transducer, and wherein said matrix material is a polymer or epoxy matrix material.

7. A soundhead according to claim 6, wherein said piezocomposite transducer is a 1-3 or 2-2 composite transducer.

8. A soundhead according to claim 5, further comprising a first electrode electrically connected to said plurality of separate ultrasound transducer elements and extending between said ultrasound transducer and said light source and a second electrode electrically connected to said plurality of separate ultrasound transducer elements and extending between said ultrasound transducer and said faceplate, wherein each of said first and second electrodes have gaps or are formed of a discontinuous layer having openings therein permitting the light from said light source to pass there through.

9. A soundhead according to claim 8, wherein said electrodes are in the form of spaced-apart lines or rings.

10. A soundhead according to claim 8, wherein said electrodes are co-extant with said plurality of separate ultrasound elements.

11. A soundhead according to claim 8, wherein one of said electrodes is in the form of concentric rings that are separately energizable whereby an ultrasound distribution pattern generated in tissue by said ultrasound transducer can be focused or defocused by changing the phase of an electric drive signal applied to the one of said electrodes.

12. A soundhead according to claim 1, wherein said faceplate is made of a plastic material that is transparent or translucent to said light produced by said topical photodynamic therapy light source.

13. A soundhead according to claim 1, further comprising a housing in or on which said topical photodynamic therapy light source, ultrasound transducer, and faceplate are mounted.

14. A soundhead according to claim 1, wherein said ultrasound transducer includes at least one ring-shaped transducer.

15. A soundhead that allows a volume of tissue located beneath the soundhead to simultaneously receive ultrasound and light stimulation, the soundhead comprising:
    an ultrasound transducer for generating ultrasound to treat the volume of tissue, the ultrasound transducer comprising a plurality of separate, spaced-apart ultrasound transducer elements embedded within a matrix material;
    a faceplate extending across a face of said transducer and configured to provide a tissue contacting and ultrasound energy coupling surface of the soundhead;
    a topical photodynamic therapy light source for producing light to treat the volume of tissue, the light having a therapeutic effect and comprising at least one of visible light, ultraviolet light, and infrared light, said light source being located on a same side of said faceplate as said ultrasound transducer; and a housing in or on which said light source, ultrasound transducer, and faceplate are mounted; said faceplate being made of a material that is transparent or translucent to the light produced by said topical photodynamic therapy light source, and said matrix material of said ultrasound transducer being transparent or translucent to the light produced by said topical photodynamic therapy light source.

16. A soundhead according to claim 15, wherein said topical photodynamic therapy light source is located adjacent a face of said ultrasound transducer opposite said faceplate such that said ultrasound transducer extends between said light source and said faceplate.

17. A soundhead according to claim 16, further comprising a first electrode electrically connected to said plurality of separate ultrasound transducer elements and extending between said ultrasound transducer and said topical photodynamic therapy light source and a second electrode electrically connected to said plurality of separate ultrasound transducer elements and extending between said ultrasonic transducer and said faceplate, wherein each of said first and second electrodes have gaps or are formed of a discontinuous layer having openings therein permitting the light from said topical photodynamic therapy light source to pass there through.

18. A method of treating a volume of tissue with ultrasound and light stimulation simultaneously, the method comprising:

generating ultrasound with an ultrasound transducer of a soundhead;

generating light with a topical photodynamic therapy light source, the light having a therapeutic effect on tissue;

contacting a faceplate of the soundhead with at least a portion of the volume of tissue, wherein the faceplate is transparent or translucent to the light produced by the topical photodynamic therapy light source; and treating the volume of tissue with the ultrasound and the light simultaneously.

19. The method of claim 18, wherein the ultrasound transducer comprises a plurality of separate, spaced-apart ultrasound transducer elements embedded within a matrix material, and wherein the matrix material is transparent or translucent to the light produced by the topical photodynamic therapy light source.

20. The method of claim 19, wherein the soundhead further comprises a first electrode electrically connected to the plurality of ultrasound transducer elements and extending between the ultrasound transducer and the topical photodynamic therapy light source, and a second electrode electrically connected to the plurality of separate ultrasound transducer elements and extending between the ultrasound transducer and the faceplate, wherein each of the first and second electrodes have gaps therein permitting the light from the topical photodynamic therapy light source to pass there through.

* * * * *